United States Patent [19]

Humphrey

[11] 4,261,981
[45] Apr. 14, 1981

[54] MEDICAL COMPOUND PRODUCED FROM RAGWEED

[76] Inventor: Sam Humphrey, 19990 Schaeffer, Detroit, Mich. 48035

[21] Appl. No.: 115,164

[22] Filed: Jan. 28, 1980

[51] Int. Cl.$^3$ ............................................. A61K 35/78
[52] U.S. Cl. ..................................................... 424/195
[58] Field of Search ........................................ 424/195

[56] References Cited

U.S. PATENT DOCUMENTS

| | | | |
|---|---|---|---|
| 73,939 | 1/1868 | Thompson | 424/195 |
| 3,935,310 | 1/1976 | Homan | 424/195 |
| 3,988,440 | 10/1976 | Bogdanov | 424/195 |

OTHER PUBLICATIONS

*Materia Medica and Therapeutics,* Sixth Ed., Ellingwood, The Ellingwood's Therapeutist Co., Chicago, pp. 634 & 635.
*Handbook of Nonprescription Drugs,* Fifth Ed., 1977, Amer. Pharm. Assoc., pp. 65–67.

*Primary Examiner*—Frederick E. Waddell
*Attorney, Agent, or Firm*—Basile, Weintraub & Hanlon

[57] ABSTRACT

A composition made from ragweed for the treatment of diarrhea, intestinal disorders, ulcers, and hemorrhoids is disclosed. A composition which effectively reduces swelling and pain in the gastro-intestinal tract and the anal area is formed by mixing ragweed leaves and water and boiling the resulting mixture in a covered container for twenty to thirty minutes. The resulting mixture may be further refined to form a salve by combining the resulting mixture with lard and boiling away the water.

4 Claims, No Drawings

MEDICAL COMPOUND PRODUCED FROM RAGWEED

BACKGROUND OF THE INVENTION

I. Field of the Invention

The present invention generally relates to the field of medicinal compounds and, in particular, the present invention is concerned with a medicinal compound formed by boiling ragweed leaves in water. Even more particularly the present invention is concerned with the treatment of hemorrhoids and intestinal disorders such as ulcers and diarrhea with a composition formed from the boiling of ragweed leaves in water.

II. Description of the Prior Art

Medical compounds formed from an aqueous solution of various plant leaves and water have long been known. Examples of medical compounds formed from plant leaves for the treatment of gastro-intestinal disorders include U.S. Pat. Nos. 073,939; and 3,988,440.

U.S. Pat. No. 073,939 uses blackberry root, ragweed leaves, and white-oak bark with minor amounts of other ingredients and alcohol for the treatment of cholera.

U.S. Pat. No. 3,988,440 discloses a preparation for the treatment of gastritis, and gastric, and duodenal ulcers which employs dried soya medium, sucrose, and dried Lactobacillus bulgaricus culture.

U.S. Pat. No. 3,935,310 discloses a remedy for the treatment of hemorrhoids which comprises a salve resulting from the heating to a temperature of 100° F. to 240° F. a mixture of powdered or chipped limbs or roots of the shrub bitter-sweet and an animal or vegetable fat. None of the above listed United States Patents disclose the use of an aqueous solution formed from the boiling of ragweed leaves in water for the treatment of intestinal disorders such as ulcers and diarrhea or the use of a salve formed from the above aqueous solution in combination with animal or vegetable fat for the relief of hemorrhoids.

III. PRIOR ART STATEMENT

The aforementioned Prior Art in the opinion of the Applicant and the Applicant's Attorney, represents the closest prior art of which the Applicant and his Attorney are aware.

SUMMARY OF THE INVENTION

The present invention, which will be described in greater detail hereinafter, comprises a medical compound for the treatment of diarrhea and intestinal disorders such as ulcers which is formed by boiling ragweed leaves of the genus ambrosia in water to form an aqueous solution. The ragweed leaves and water are boiled for twenty to thirty minutes then the leaves and solids are strained from the boiled mixture. The resulting mixture may be consumed internally in small quantities for the relief of intestinal disorders such as diarrhea and ulcers.

A salve for the treatment of hemorrhoids is formed by boiling ragweed leaves in water for twenty to thirty minutes to form an aqueous solution; straining the solids from the boiled mixture; adding lard or vegetable fat to the boiled mixture; and boiling away the water to form a salve. The resulting salve may be used effectively to relieve hemorrhoids by applying the salve to diseased tissue in the anal area.

It is therefore an object of the present invention to use ragweed leaves for the treatment of gastro-intestinal disorders and the relief of pain resulting therefrom.

It is also an object of the present invention to provide a medical compound for the treatment of diarrhea.

It is a further object of the present invention to provide a medical compound using ragweed leaves for the relief of pain resulting from gastric and duodenal ulcers.

It is additionally an object of the present invention to provide a medical compound in the form of a salve using the leaves of ragweed for the relief of the pain of hemorrhoids.

Other objects, advantages, and applications of the present invention will become apparent to those skilled in the field to which this invention pertains, when reading the accompanying description of the best modes contemplated for practicing the invention.

DESCRIPTION OF THE PREFERRED EMBODIMENT

The affect of pollen from the plant known as ragweed upon the sinuses of humans which results in the disease known as hayfever has long been known. I have discovered that an aqueous solution formed from the boiling of the ragweed leaves in water for twenty to thirty minutes in a covered pot has an unusually beneficial effect on persons suffering from ulcers, diarrhea, and similar gastro-intestinal disorders. The aqueous solution formed from the boiling of ragweed leaves from a plant of the genus ambrosia when taken internally in one ounce doses three times a day preferably before meals, relieves the pain and symptoms resulting from diarrhea, ulcers, and other gastrointestinal disorders. If the pain and symptoms are not relieved shortly after using solution as outlined above, the person suffering from these disorders should consult his physician.

In a preferred embodiment a composition for the treatment of and the relief of the pain of diarrhea and intestinal disorders such as ulcers is formed by combining the steps of:

cutting five pounds of ragweed leaves of the genus ambrosia into pieces approximately one to two inches long;

mixing the cut ragweed leaves into one gallon of water;

boiling the mixture in a covered container for twenty to thirty minutes;

straining the solids from the boiled mixture; and storing the resulting composition in a covered container in a cool place until use.

The aqueous solution as produced above has the unusual affect of reducing swelling and pain when it occurs in the delicate membranes of the gastro-intestinal tract when taken internally by consumption in one ounce doses three times daily, preferably before meals.

A salve for the treatment of hemorrhoids may be formed utilizing ragweed leaves by combining the steps of:

cutting five pounds of ragweed leaves of the genus ambrosia into pieces of approximately one to two inches long;

mixing the cut ragweed leaves into one gallon of water;

boiling the mixture in a covered container for twenty to thirty minutes;

straining the solids from the boiled mixture;

mixing one half gallon of the boiled mixture with five pounds of lard or vegetable fat;

boiling the mixture until all water is removed; and storing the mixture in a covered container in a cool place.

The resulting salve from the above steps may be applied to the swollen blood vessels in the anal area resulting from hemorrhoids twice daily, and the user should obtain almost immediately relief. Should the pain and discomfort from the hemorrhoids persist, the user should consult his physician.

It can thus be seen that the present invention has provided a new and improved composition for the treatment of diarrhea and intestinal disorders such as ulcers that can result in immediate and lasting relief.

It can also be seen that the present invention has provided a new and improved salve for the treatment of hemorrhoids that can result in lasting relief from this disease when the salve is applied to the affected areas.

It should be understood by those skilled in the art to which this invention pertains that other forms of the Applicant's invention may be had, all coming within the spirit of the invention and the scope of the appended claims.

Having thus described my invention what I claim is:

1. A medical composition for the treatment of diarrhea and intestinal ulcers consisting essentially of an aqueous solution of Genus Ambrosia which is prepared by:
   cutting ragweed leaves of the Genus Ambrosia into discrete pieces approximately one to two inches long;
   mixing the cut ragweed into water;
   boiling the mixture in a covered container for twenty to thirty minutes;
   straining the solids from the mixture;
   storing the resulting composition in a covered container in a cool place; and
   wherein approximately five pounds of leaves are employed per gallon of water.

2. A method of treating diarrhea and intestinal ulcers in a patient comprising internally administering by consumption one ounce of the composition of claim 1 three times daily preferably before meals until the condition is corrected.

3. A salve for the treatment of hemorrhoids prepared by:
   cutting five pounds of ragweed leaves of the Genus Ambrosia into discrete pieces approximately one to two inches long;
   mixing the cut ragweed leaves into one gallon of water;
   boiling the mixture in a covered container for twenty to thirty minutes;
   straining the solids from the boiled mixture;
   mixing one half gallon of the boiled mixture with five pounds of lard or vegetable shortening;
   boiling and dehydrating the mixture until all water is removed producing a salve; and
   storing the salve in a covered container in a cool place.

4. A method for relieving the pain and swelling of hemorrhoids in a patient comprising the step of topically applying an effective amount of the salve of claim 3 to the swollen blood vessels in the anal area twice daily until the condition is corrected.

* * * * *